(12) United States Patent
Amparo Pulido

(10) Patent No.: US 12,357,176 B2
(45) Date of Patent: Jul. 15, 2025

(54) SYSTEM AND METHOD FOR ACQUISITION AND QUANTIFICATION OF IMAGES WITH OCULAR STAINING

(71) Applicant: Boston Eye Diagnostics, Inc., Boston, MA (US)

(72) Inventor: Francisco Leonardo Amparo Pulido, Boston, MA (US)

(73) Assignee: BOSTON EYE DIAGNOSTICS, INC., Boston, MA (US)

( * ) Notice: Subject to any disclaimer, the term of this patent is extended or adjusted under 35 U.S.C. 154(b) by 0 days.

(21) Appl. No.: 18/005,710

(22) PCT Filed: Jul. 15, 2021

(86) PCT No.: PCT/US2021/041727
§ 371 (c)(1),
(2) Date: Jan. 17, 2023

(87) PCT Pub. No.: WO2022/015915
PCT Pub. Date: Jan. 20, 2022

(65) Prior Publication Data
US 2023/0284903 A1  Sep. 14, 2023

Related U.S. Application Data

(60) Provisional application No. 63/052,891, filed on Jul. 16, 2020.

(51) Int. Cl.
*A61B 3/117* (2006.01)
*A61B 3/15* (2006.01)
(Continued)

(52) U.S. Cl.
CPC ............ *A61B 3/152* (2013.01); *A61B 5/1075* (2013.01); *A61B 5/1079* (2013.01); *A61K 49/0013* (2013.01)

(58) Field of Classification Search
CPC .............................. A61B 3/152; A61B 5/1075
(Continued)

(56) References Cited

U.S. PATENT DOCUMENTS

2013/0230259 A1\* 9/2013 Intwala ................... G06T 11/00
382/255
2015/0085253 A1\* 3/2015 Walsh ...................... A61B 3/18
351/208
(Continued)

FOREIGN PATENT DOCUMENTS

CN 209285469 U 8/2019
EP 3136947 A1 3/2017
WO WO-2018013923 A1 \* 1/2018 ............. A61B 3/028

OTHER PUBLICATIONS

International Search Report and Written Opinion for International Application No. PCT/US21/041727, mailed Oct. 16, 2024.

*Primary Examiner* — Nguyen T Truong
(74) *Attorney, Agent, or Firm* — Nieves IP Law Group, LLC; Peter A. Nieves

(57) ABSTRACT

A system for determining a staining score of portions of dyeable epithelia within the ocular surface of a subject includes a portable computing device with a camera, a display, a memory, and a processor configured to execute a staining score application. An illumination/optics device with a light source and optics is configured to receive an image of the ocular surface. The illumination/optics device may be removably attached to the portable computing device. The staining score application includes an alignment module, an image acquisition module, and a staining scoring module.

17 Claims, 12 Drawing Sheets

(51) Int. Cl.
  *A61B 5/107* (2006.01)
  *A61K 49/00* (2006.01)
(58) Field of Classification Search
  USPC .......................................................... 348/46
  See application file for complete search history.

(56) References Cited

U.S. PATENT DOCUMENTS

2020/0107715 A1* 4/2020 Dana .................... A61B 5/4848
2020/0163545 A1  5/2020 Fukuma et al.

* cited by examiner

ND QUANTIFICATION OF IMAGES WITH
SYSTEM AND METHOD FOR ACQUISITION AND QUANTIFICATION OF IMAGES WITH OCULAR STAINING

CROSS-REFERENCE TO RELATED APPLICATIONS

This application claims the benefit of U.S. Provisional patent application Ser. No. 63/052,891, filed Jul. 16, 2020, entitled "Acquisition and quantification of images with Corneal Fluorescein Staining," which is incorporated by reference herein in its entirety.

FIELD OF THE INVENTION

The present invention relates to an image acquisition and processing device for the evaluation of the eye, and more particularly to an instrument that permits accurate evaluation and measurement of corneal and conjunctival diseases.

BACKGROUND OF THE INVENTION

There is currently no "gold standard" for dry eye disease (DED) and other ocular surface diseases assessment. Clinical evaluation relies on a combination of signs and symptoms to stratify the severity of the disease. Key dry eye assessments include corneal fluorescein staining (CFS) and other vital dyes (e.g., lissamine green, rose bengal) to visualize devitalized areas of corneal or conjunctival epithelium, patient-reported symptoms, tear film break-up time (TBUT), and tear osmolarity. Subjective assessment is common in the majority of DED tests and discrepancies among these are likely attributable to the lack of test standardization and well-defined diagnostic criteria or to the heterogeneity of DED itself. Also, discrepancies between symptom surveys and clinical signs are a characteristic of DED, and can further complicate DED evaluations. However, severe DED is diagnosed based on two criteria: CFS scoring and patient symptoms.

CFS is the most meaningful clinical assessment of DED, and it is required by the US Food and Drug Administration (FDA) as one of the main endpoints in clinical trials for DED therapeutics or diagnostic devices. CFS reveals devitalized areas of the corneal epithelium (wounded epithelium) and areas of inflammation by the use of fluorescein dye over the ocular surface. CFS scores are used to guide medical diagnoses, management, and to evaluate the effects of therapy. Currently, clinicians perform CFS tests by subjectively assessing distribution and intensity of fluorescein infiltration in the corneal epithelium in the form of green punctate staining using a slit lamp biomicroscope under blue illumination, and in very rare occasions (e.g., some clinical trials) contrasting their observations with a printed score chart of available CFS scoring systems (e.g., NEI, Oxford). The incremental scale categories of the National Eye Institute (NEI) and Oxford CFS scoring systems are not continuous and are only roughly quantifiable. Small increments of DED improvement or worsening are not captured in these scoring systems and are easily missed; also, severe cases of the disease can fall outside the range of such score systems. These subjective measurement scales are inherently prone to variability between doctors in different clinical practices and potentially even between different readings by the same clinician. Therefore, there is a need in the industry to address one or more of the abovementioned shortcomings.

SUMMARY OF THE INVENTION

Embodiments of the present invention provide a system and method for acquisition and quantification of images with ocular staining. Briefly described, the present invention is directed to a system for determining a staining score for portions of dyeable epithelia within the ocular surface of a subject. A portable computing device with a camera, a display, a memory, and a processor, is configured to execute a staining score application. An illumination/optics device with a light source and optics is configured to receive an image of the ocular surface. The illumination/optics device may be removably attached to the portable computing device. The staining score application includes an alignment module, an image acquisition module, and a staining scoring module.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principles of the invention.

DETAILED DESCRIPTION

Figure 1:
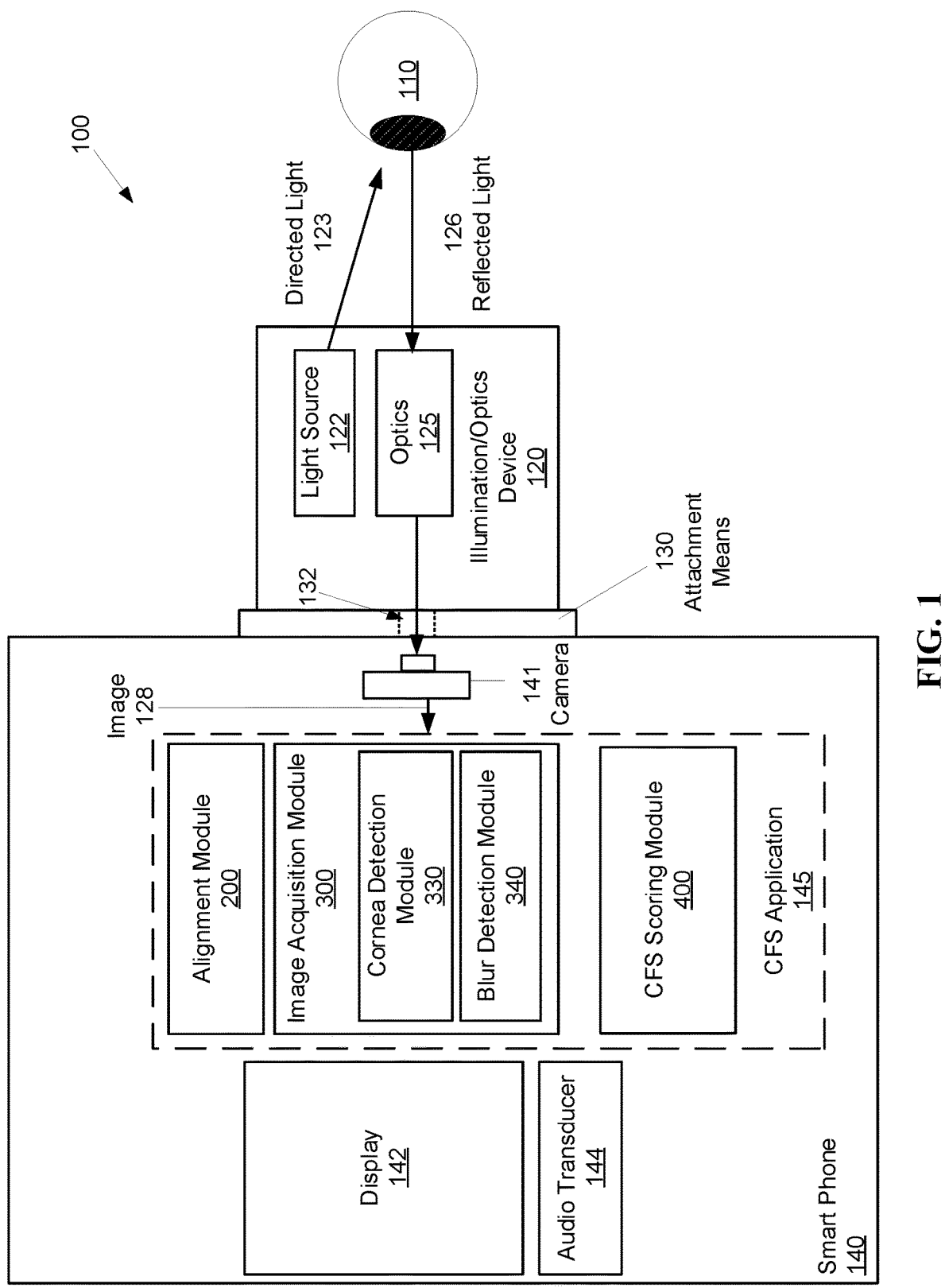
FIG. 1 is a schematic block diagram of a first exemplary embodiment of a system for the acquisition and quantification of images with corneal fluorescein staining.

The following definitions are useful for interpreting terms applied to features of the embodiments disclosed herein, and are meant only to define elements within the disclosure.

As used within this disclosure, "blur" refers to an image or area of an image where the color transition from one side of an edge in the image to another is smooth rather than sharp. Blur may be calculated evaluating the differences between contiguous pixels in a local region of pixels.

As used within this disclosure, a "spatial window" refers to a region in an image of local contiguous pixels defined by a geometric shape for example a square or rectangle of dimensions m×n, or a circle of radius r.

As used within this disclosure, "score" refers to a measure of an amount of staining of the cornea in an image of an eye. The eye is stained with a tracer material such as fluorescein, which reacts with certain wavelengths directed upon the eye. The score is assigned to portions (pixels) of the image based upon hue and location (region).

As used within this disclosure, a "dyeable epithelia" refers to a plurality of epithelia cells receptive to a tracer material, for example, a fluorescein dye.

As used within this disclosure a "Wiener filter" refers to a filter used to produce an estimate of a desired or target random process by linear time-invariant (LTI) filtering of an observed noisy process, assuming known stationary signal and noise spectra, and additive noise. The Wiener filter minimizes the mean square error between the estimated random process and the desired process.

As used within this disclosure, an "image pyramid" refers to is a type of multi-scale signal representation of an image in which the image is subject to repeated smoothing and subsampling.

Reference will now be made in detail to embodiments of the present invention, examples of which are illustrated in the accompanying drawings. Wherever possible, the same reference numbers are used in the drawings and the description to refer to the same or like parts.

Exemplary embodiments of the present invention are directed to a system and method for acquisition and quantification of images with corneal fluorescein staining. In a first exemplary embodiment, a smart phone-based system includes a light source attached to the smart phone, where the smart phone hosts an application configured to (1) align a camera of the smart phone with an eye of a subject, (2) acquire a plurality of images of the eye, and (3) determine a CFS score based on the plurality of images. Exemplary embodiments of methods for the camera alignment, image acquisition, and determining of the CFS score are presented.

FIG. 1 is a schematic block diagram of a first exemplary embodiment of a system 100 for the present invention. An illumination/optics device 120 is attached to a smart phone 140 via attachment means 130, for example, via an adhesive, fasteners, straps, among other possibilities. The illumination/optics device 120 includes a light source 122 used to illuminate an eye of a subject 110. Optics 125, for example one or more lenses, receive reflected light from the eye of the subject 110 and provide an image 128 of the eye 110 to a camera 141 of the smart phone 140. The attachment means may provide an aperture and/or conduit 132 to convey an image 128 of the eye 110 to the camera 112.

As described below, the light source 122 may be internal to the illumination/optics device 120, or may be external to the light/optics device 120. The illumination/optics device 120 may interface directly with the eye of the subject 110, or the illumination/optics device 120 may be attached to one or more additional devices (not shown) providing illumination, optics and/or subject positioning that convey light between the eye of the subject 110 and the illumination/optics device 120.

Besides the camera 141, the smart phone 140 includes a display 142, for example a touch screen having a graphical user interface, and an audio transducer 144, for example one or more speakers to provide audible content such as alarms and/or spoken instructions. Alternatively, the smart phone may provide audible content via wired or wireless external devices, such as a Bluetooth speaker, headphones, or ear buds. The smartphone 140 hosts a CFS Application 145 including modules performing CFS functionality such as an alignment module 200, an image acquisition module 300, and a CFS scoring module, each of which is described in detail below. In alternative embodiments other devices may provide the functionality of the smart phone 140 of FIG. 1, for example, but not limited to a tablet computer, a laptop computer, or a desktop computer. In alternative embodiments the CFS application 145 may be hosted remotely from the smartphone 140, for example, the CFS application 145 may be hosted by a cloud-based server (not shown).

Figure 2:
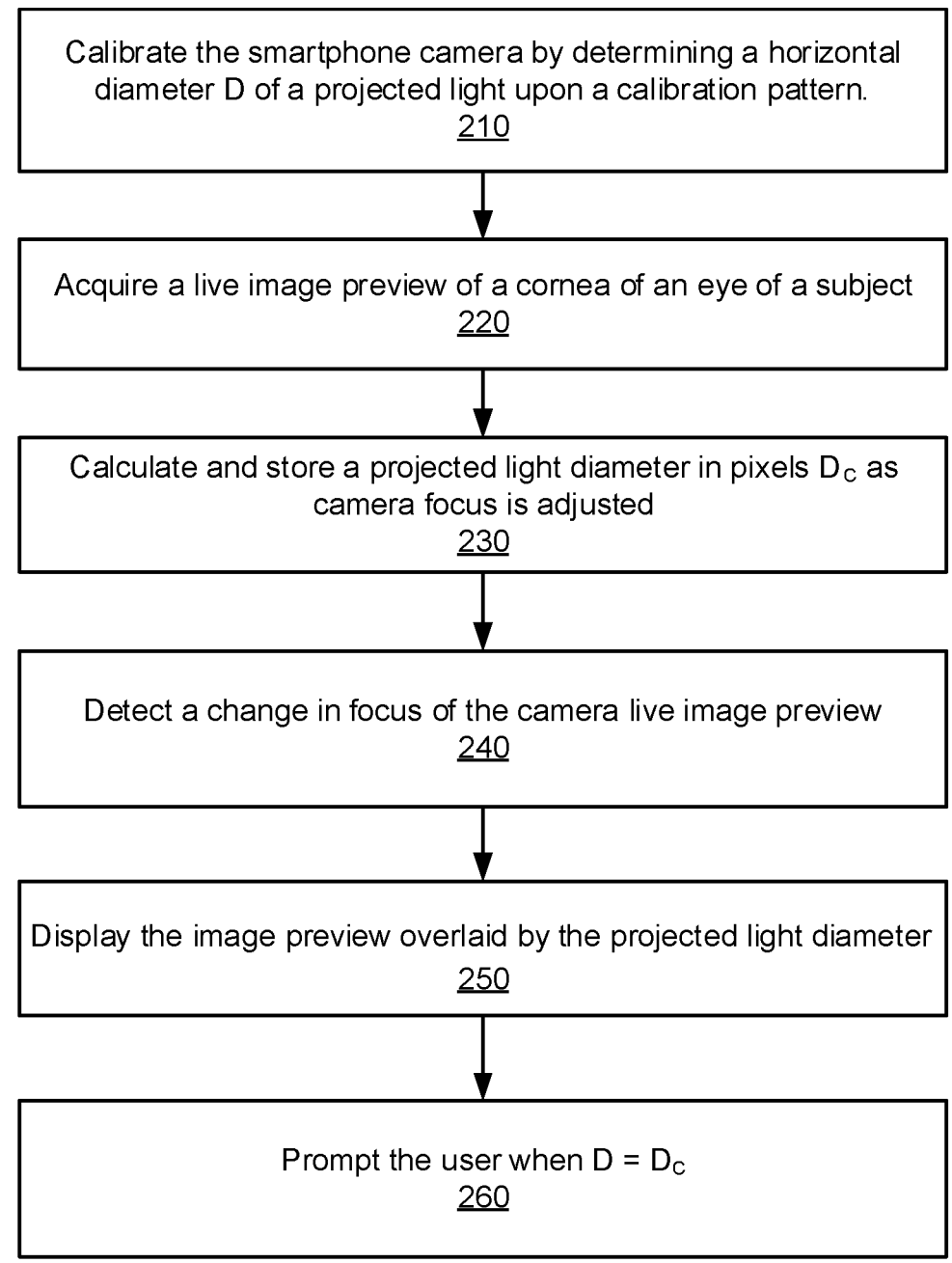
FIG. 2 is a flowchart of an exemplary method embodiment for image alignment.

FIG. 2 is a flowchart of an exemplary method embodiment for the alignment tool 200. It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention. The method is described in context of the system 100 shown in FIG. 1.

The camera 141 is calibrated, as shown by block 210. For example, a circular calibration pattern of a known size may be placed in front of the camera, the light source 122 (FIG. 1) projects a circular shape of a known color on the calibration pattern, the user moves the illumination/optics device 120 nearer or farther to obtain focus of the calibration pattern. The user may indicate the pattern is in focus, for example, by pressing a button on the smartphone 140 or a virtual button presented by the graphical user interface (GUI) on the display 142. It should be noted the calibration is typically performed at the beginning of image acquisition, and is generally not needed to acquire each subsequent image.

The illumination/optics device provides an image of the projected circular shape on the calibration pattern to the alignment module 200. The alignment module 200 segments the image by identifying the known color of the projected light and calculating the projected light diameter in pixels based upon the size of the projected light with respect to the calibration pattern. The alignment module 200 stores a calculated horizontal diameter D of the light projection. For example, calculating the projected diameter in pixels of blue projected circular light may be done by extracting a blue color channel, setting pixel intensity threshold values, creating a binary mask of pixels with high blue intensity, removing noise by eroding/dilating the mask, removing additional disconnected areas that are smaller than a size threshold, fitting an ellipse shape to the edge of the detected area, and calculating the horizontal diameter in pixels for the ellipse that best fits the detected area.

The user starts acquisition of an image of a cornea of an eye of a subject, starting with a live image preview displayed by the display 142, as shown by block 220. A diameter of the projected light Dc is calculated (as described above), updated, and stored as the camera focus is adjusted, as shown by block 230. The alignment module detects a change in focus on the cornea, as shown by block 240, for example, when the user utilizes the camera to focus on the cornea. For example, a change in focus may be detected by comparing the real-time projected light diameter with the diameter that was calculated for the optimal focus during the calibration.

An overlaid representation of the projected light diameter upon the image preview is displayed with the display 142, as shown by block 250. The user is prompted to acquire the image only when Dc=D, for example, by changing a color of the overlay circle as shown by block 260, such as from red to green.

Figure 3A:
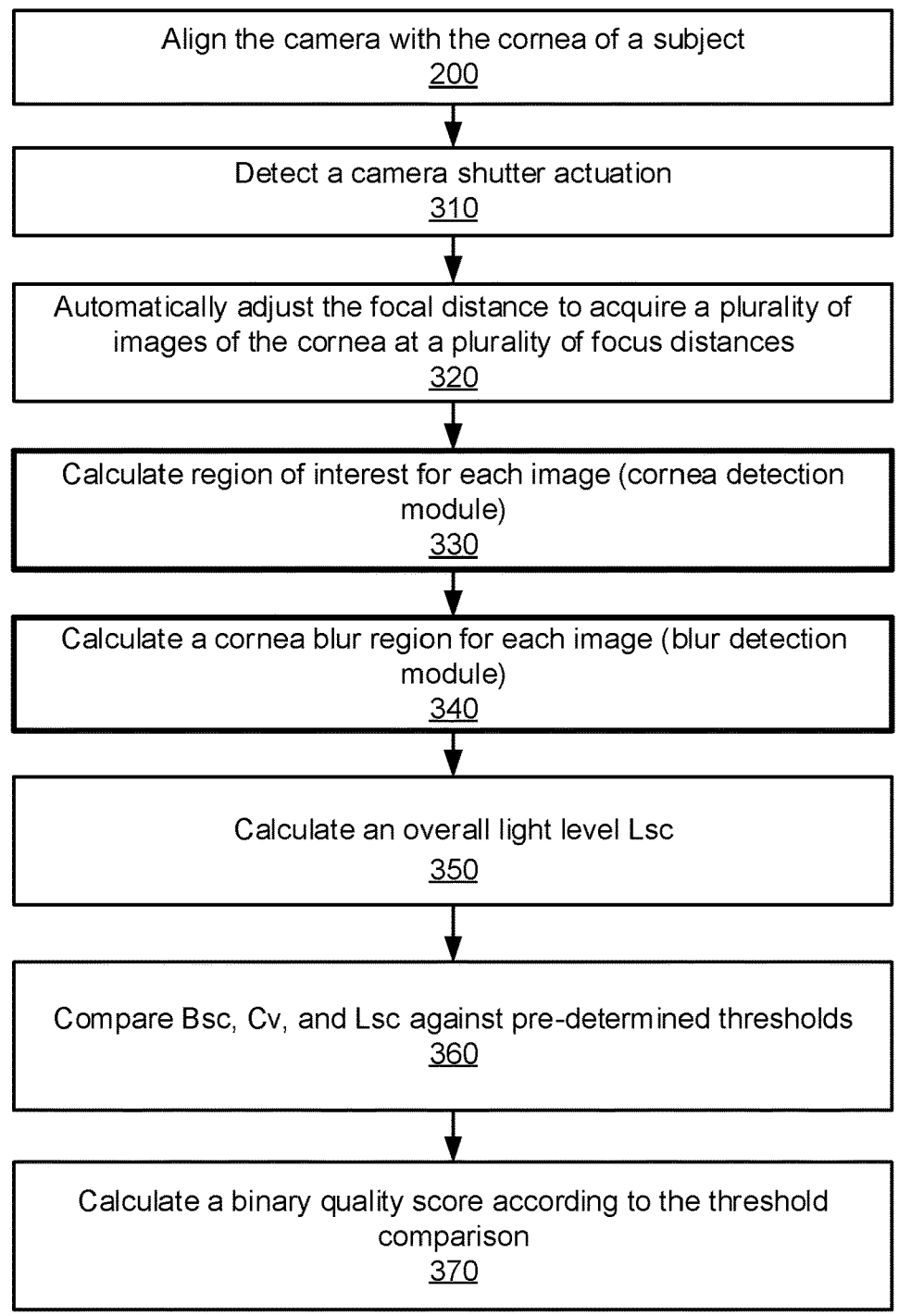
FIG. 3A is a flowchart of an exemplary method embodiment for image acquisition.

FIG. 3A is a flowchart of an exemplary method embodiment for the image acquisition tool 300. The camera is aligned with the cornea of a subject, as shown in block 200 and expanded in FIG. 2, described above. Initially, the camera 142 is set to a fixed focus, exposure, and ISO. For example, for an iPhone SE2, having a lens position of 0.6, an ISO of 120, and an exposure of ⅓₀. After alignment and focus, a user press of a shutter button of the camera is detected, as shown by block 310. The camera acquires a plurality of images of the cornea at a plurality of focal distance to compensate for the curvature of the cornea and ocular surface, as shown by block 320. For example, the image acquisition tool may automatically vary the focal distance from the manually set focal distance, so the plurality of images includes a first image having a focal distance according to the manually set focal distance, a second image having a second, shorter focal distance than the first image, and a third image having a third focal distance longer than the first image. For example, the number of images may be three, with the second image having a focal distance 1.5 mm shorter than the first image, and the third image having a focal distance 1.5 mm longer than the first image. While three images are collected for this example, alternatively the plurality of images may include 2, 4, 5, 6, or more images, and the focal distance may be more or less than 1.5 mm between each image. The difference between focal distances between consecutive images need not be equal.

Figure 3B:
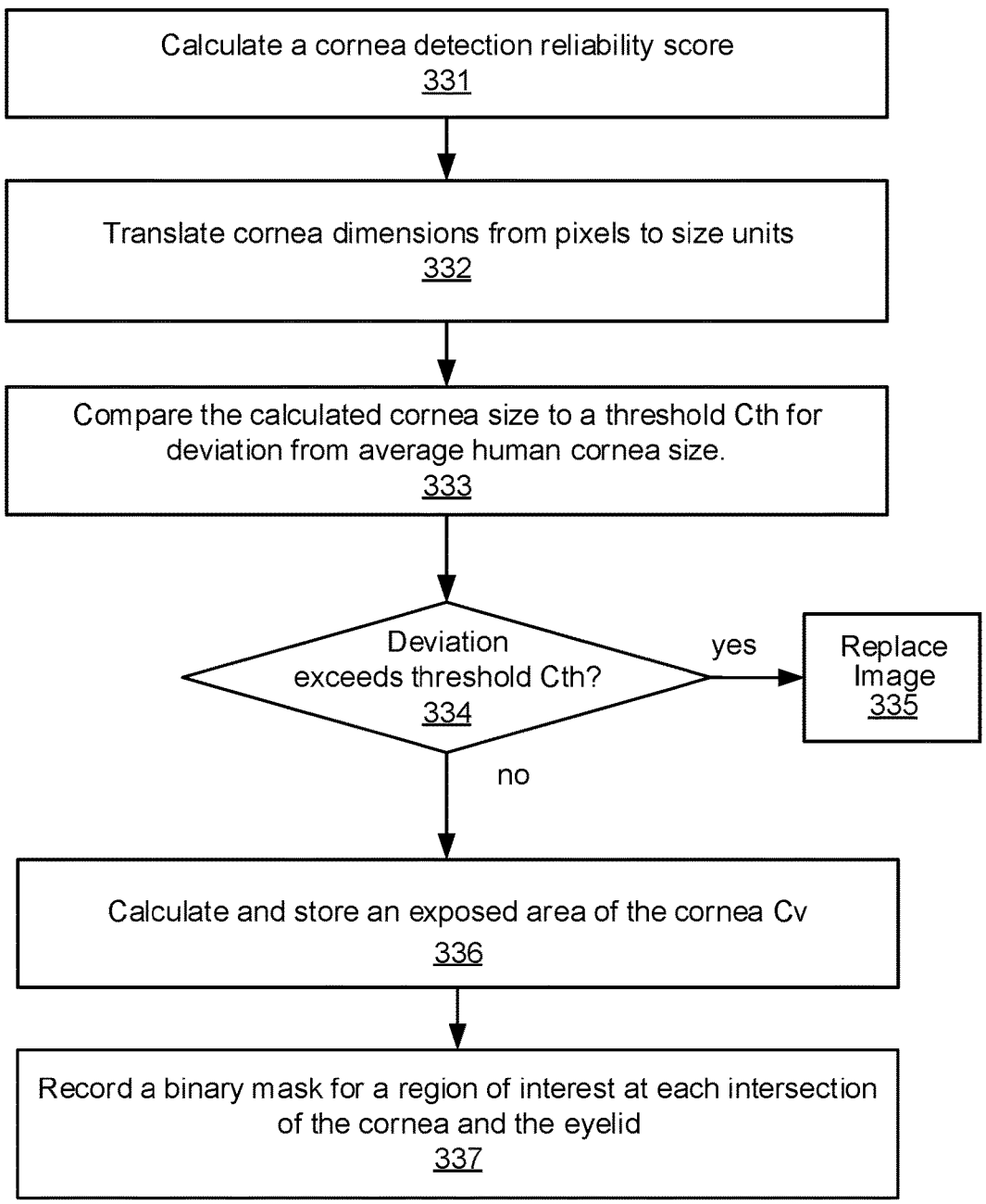
FIG. 3B is a flowchart detailing the cornea detection module of FIG. 3A.

A cornea detection module calculates the region of interest for each of the images, as shown by block 330, expanded in FIG. 3B. The cornea detection module 330 applies a deep learning methodology. A cornea detection reliability score is calculated based on a horizontal size and a vertical size of the cornea shape as shown by block 331, and described further below. The horizontal and vertical sizes are translated from pixels to size units (for example, mm) using the calibration factor obtained in the initial calibration, as shown by block 332. As shown by block 333, the calculated cornea size is compared with the average size of a human cornea, and a deviation in size of the calculated cornea greater than a threshold Cth prompts the user for re-acquisition of the image, as shown by blocks 334-335. The cornea boundaries together with the boundaries of the eyelids are used to calculate the area of the cornea that is exposed and not covered by the eyelids, as shown by block 336. The percentage of the cornea visible is stored as Cv. For each image, a region of interest is recorded as a binary region of interest mask based on the intersection of the cornea and the eyelid detection, as shown by block 337.

Figure 3C:
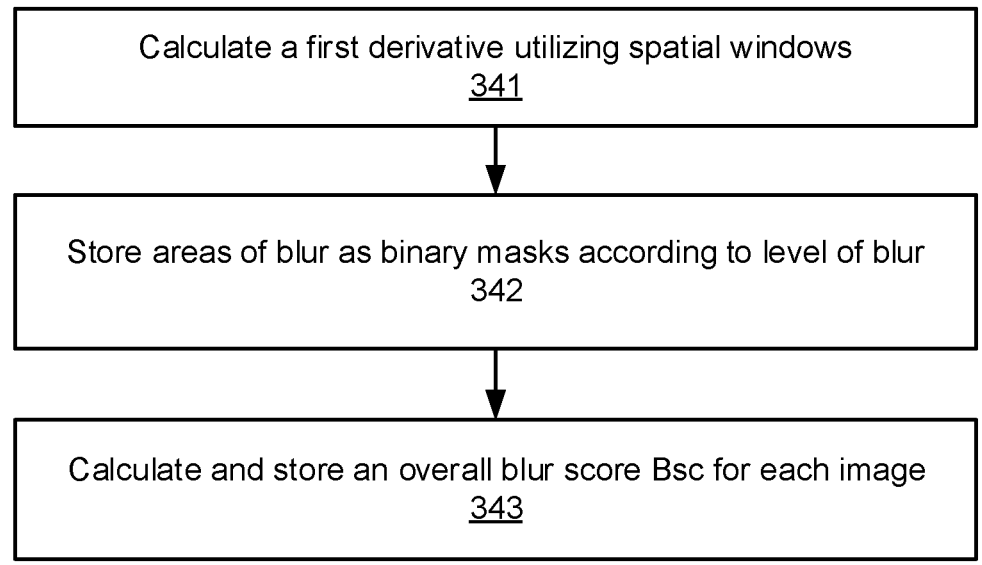
FIG. 3C is a flowchart detailing the blur detection module of FIG. 3A.

A blur in the cornea region is calculated for each of the images, as shown by block 340, expanded in FIG. 3C. The blur detection method is based on an analysis of the 2D derivative function of the image. The first derivative is calculated utilizing different spatial windows as shown by block 341, for a non-limiting example, from 5 to 15 pixels. The first derivative as a function of the window size indicates blur when the function has plateaued at a predetermined threshold Bth. The areas of less blur are stored as binary masks, as shown by block 342. The binary blur masks are used for Corneal Fluorescein Staining image segmentation, described later. An overall blur score is calculated for each image as the average of the blur score for all the pixels in the region of interest and stored as Bsc, as shown by block 343. An overall light level is calculated in each of the acquired images, as shown by block 340, where the RGB images are converted into grayscale, a mean of all the grayscale is calculated, and the mean value is normalized and stored as Lsc. The blur score Bsc, the percentage of the cornea exposed Cv, and the light level Lsc are compared against predetermined thresholds, as shown by block 360. As non-limiting examples, the light level threshold may be 0.1, the cornea reliability threshold may be 0.12, the blur reliability threshold may be 0.6, and the percentage of cornea visible threshold may be 0.9.

A binary quality score is calculated, for example, as the logical AND operation between blur, light, and cornea exposed thresholding result, as shown by block 370. In case of an insufficient quality score, the module 300 directs the user to re-acquire the images providing feedback on which of the scores was not sufficient. In case of a sufficient quality score, the images are stored and sent to the CFS processing module 400 together with the region of interest masks.

Given the curvature of the cornea and the high magnification level in slit-lamps, a traditional image acquisition does not have a sufficient depth of focus to clearly define high-frequency signals like the punctate in a CFS image. When focusing on the center of the cornea the pixels at the boundary are slightly blurred causing the effect of low-pass optical filtering for the pixels out of focus. The image acquisition module 300 provides a time-controlled acquisition of multiple images in raw format at different depths of focus regulated progressively by the smartphone processor. During this step, the image acquisition module 300 triggers at the press of the shutter button on the main screen and captures multiple images at different focal lengths. The raw format images are then combined by the processor into a single one for its ulterior processing. The final image takes different parts of the cornea from a different image. The final pixel values P are calculated as a linear combination between the correspondent pixel location in the images acquired. Each of the components is weighted accordingly to the distance d from the center of the cornea. Eq. 1:

$$P_{ij} = \sum_{i=x_0; j=y_0; D=0}^{i=X; y=Y; D=N} w_D p_{ijD}$$

$i, j \in C$ where $C$ is the cornea region of interest $$w_D = \begin{cases} 1 - \dfrac{\left|d - \dfrac{D}{N}\right|}{\dfrac{1}{N}} & \text{if } \max\left(0, \dfrac{D-1}{N}\right) \leq d < \min\left(1, \dfrac{D+1}{N}\right) \\ 0 & \text{otherwise} \end{cases}$$

$$d_{ij} = \frac{\sqrt[2]{(x_i - x_0)^2 + (y_j + y_0)^2}}{R}$$

Where D is the index of the weight, N is the number of images acquired, and R is the radius of the cornea region in pixels used to normalize the distances $d_{ij}$. As a final outcome, pixels from the center of the cornea rely more on the image with the shorter focus distance and pixels at the cornea boundary rely instead on the image with the longer focus distance.

The image processing code runs locally in a smartphone and/or a remote server and follows the image acquisition. The image is acquired and processed in the raw format without lossy compression or acquisition artifacts and beautifications. The image processing code may be adapted for mobile processors. The present embodiment is described with respect to Apple® IOS devices, but is also applicable to Android and other operating systems. The code for iOS may be implemented using a procedural computer programming language integrated with Objective C (Apple®) developed using the Xcode programming environment. In general terms, the image processing provides:

pre-processing, including filtering, color space conversion, and calculation of image histogram.

evaluation and suppression of determining color components, enhancement of greenness, and calculation of the pixel-wise green score.

Post-processing, including smoothing and gamma correction.

Figure 4:
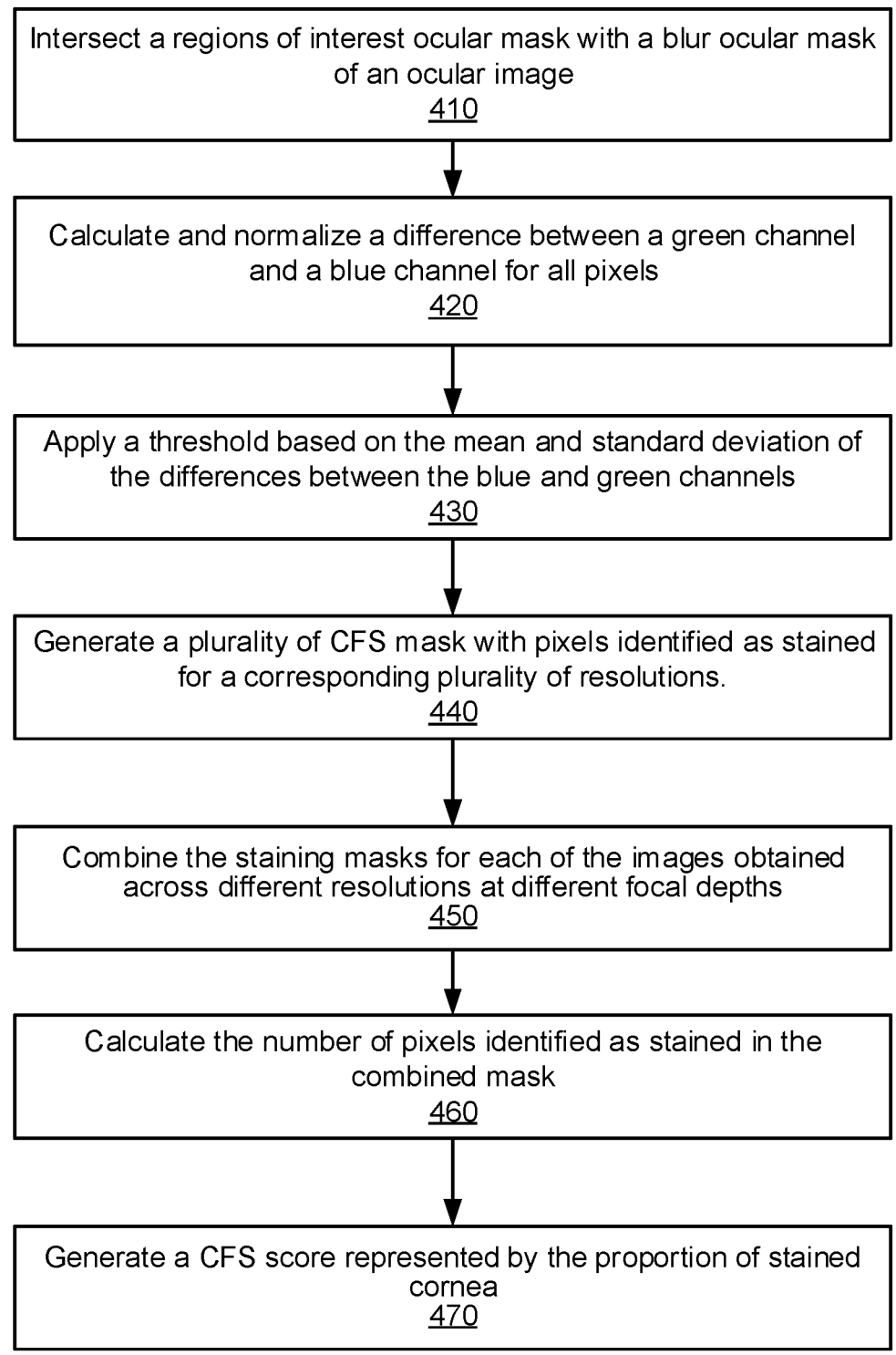
FIG. 4 is a flowchart of an exemplary method embodiment for CFS scoring.

FIG. 4A is a flowchart of an exemplary method embodiment for the CFA scoring tool 400. The region of interest mask (FIG. 3B, block 337) is intersected with the blur mask (block 242), as shown by block 410. The difference between green (G) and blue (B) channels is calculated and normalized for all the pixels, as shown by block 420. Apply a threshold based on the mean and standard deviation of the differences between the blue and green channels, as shown by block 430. The threshold may be automatically determined as described further below.

A plurality of CFS masks is generated for a plurality of resolutions (scales), where each mask consists of the pixels identified as stained, as shown by block 440. Generating the CFS mask further entails calculating the differences between the center pixel and the surrounding pixels in a window of a specific size for a specific color channel, for example, a window size of 5×5 for the green channel. Each pixel with a difference between the center and the surround larger than a threshold is categorized as a candidate for the CFS scoring. For example, the image resolutions (scales) may range from 12 Megapixels images with resolution 3024×4032 for the largest scale (full size), to smaller scales such as 1512×2016, 756×1008, and 379×504. The staining masks are combined for each of the images obtained across different resolutions and at different focal depths as shown by block 450, for example with a logical AND operation. The number of pixels identified as stained in the combined mask is calculated, as shown by block 460. A CFS score is calculated representing the percentage of cornea stained, as shown by block 470, for example, by determining the total number of pixels stained over total number of pixels in the cornea region of interest.

Figure 6:
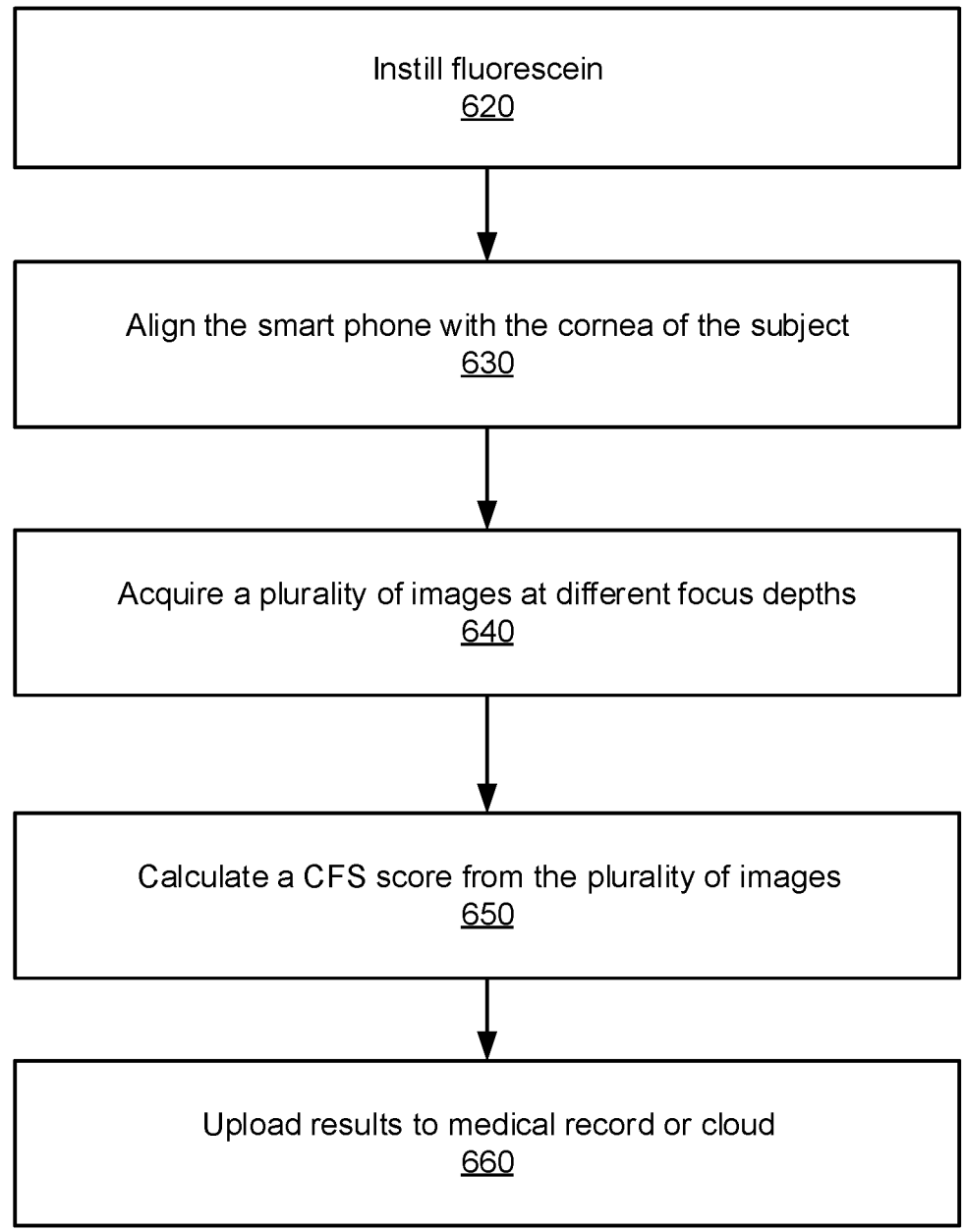
FIG. 6 is a flowchart of an exemplary method embodiment for using the system of FIG. 1.
Figure 9:
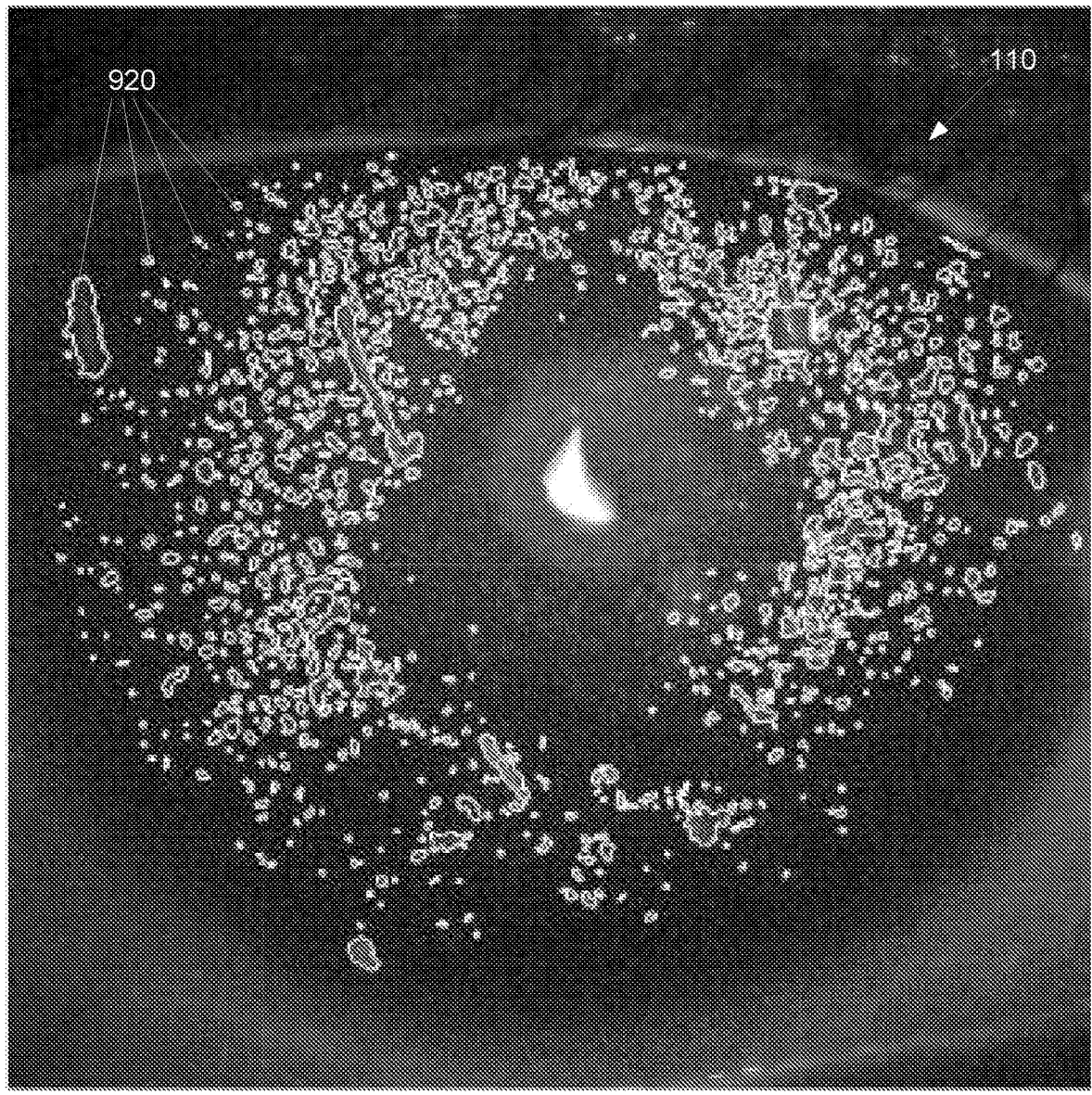
FIG. 9 is an image depicting an example of segmentation for stained areas of an ocular image when using fluorescein.

FIG. 6 is a flowchart of an exemplary method embodiment for using the system of FIG. 1, with reference to the above described exemplary method embodiments. A tracing medium, such as fluorescein is instilled in the eye of the subject 620, as shown by block 620. The smart phone 140 and illumination/optics device 120 are aligned with the eye of a subject 110, as shown by block 630. A plurality of images is acquired at different focus depths, as shown by block 640. A CFS score is calculated from the plurality of images, as shown by block 650. FIG. 9 depicts an example of segmentation for stained areas 920 of an ocular image 900 when using fluorescein. The CFS score is uploaded to a medical record and/or to a cloud server, as shown by block 660.

Figure 7A:
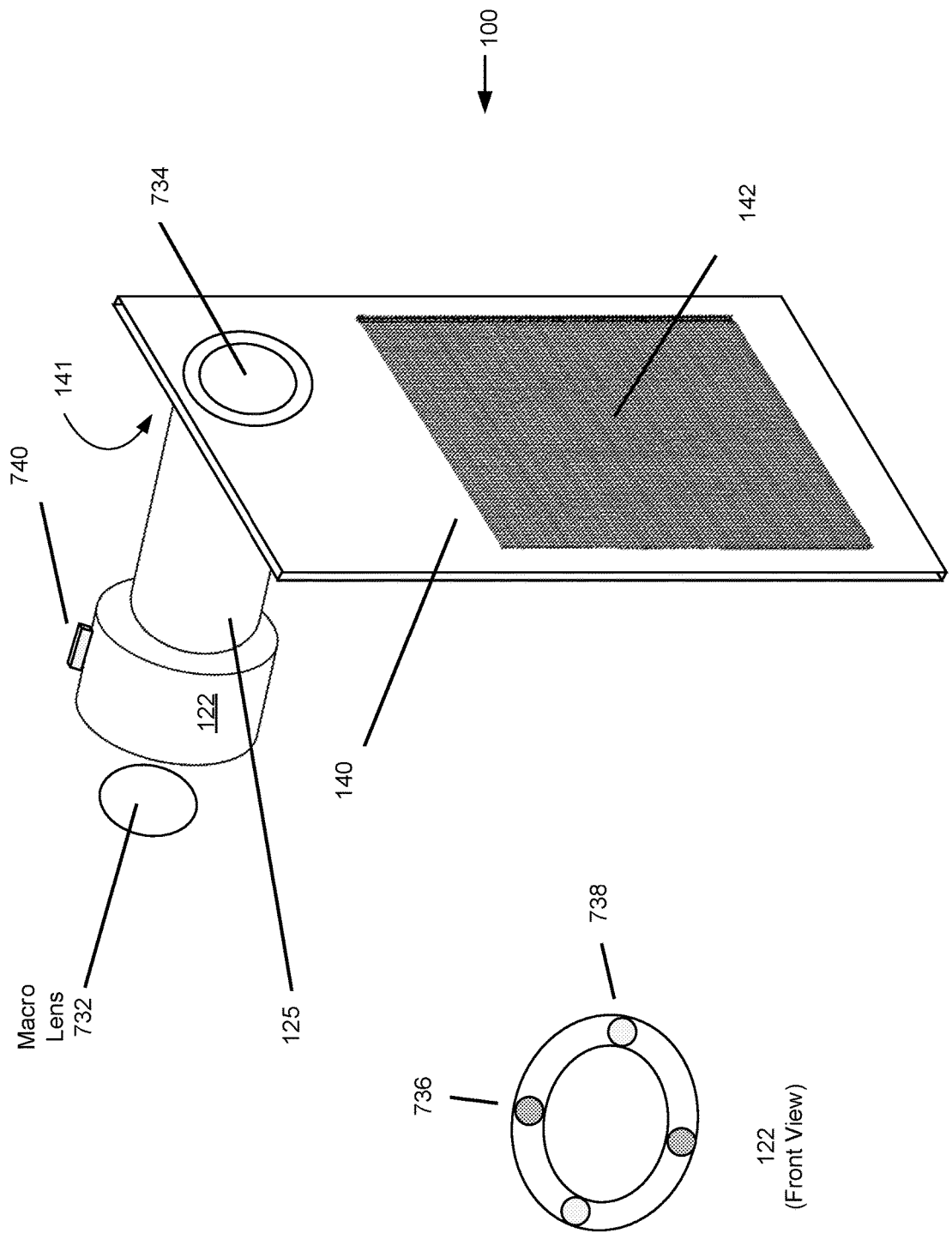
FIG. 7A is a schematic diagram of an exemplary embodiment of the illumination/optics device of FIG. 1.
Figure 7B:
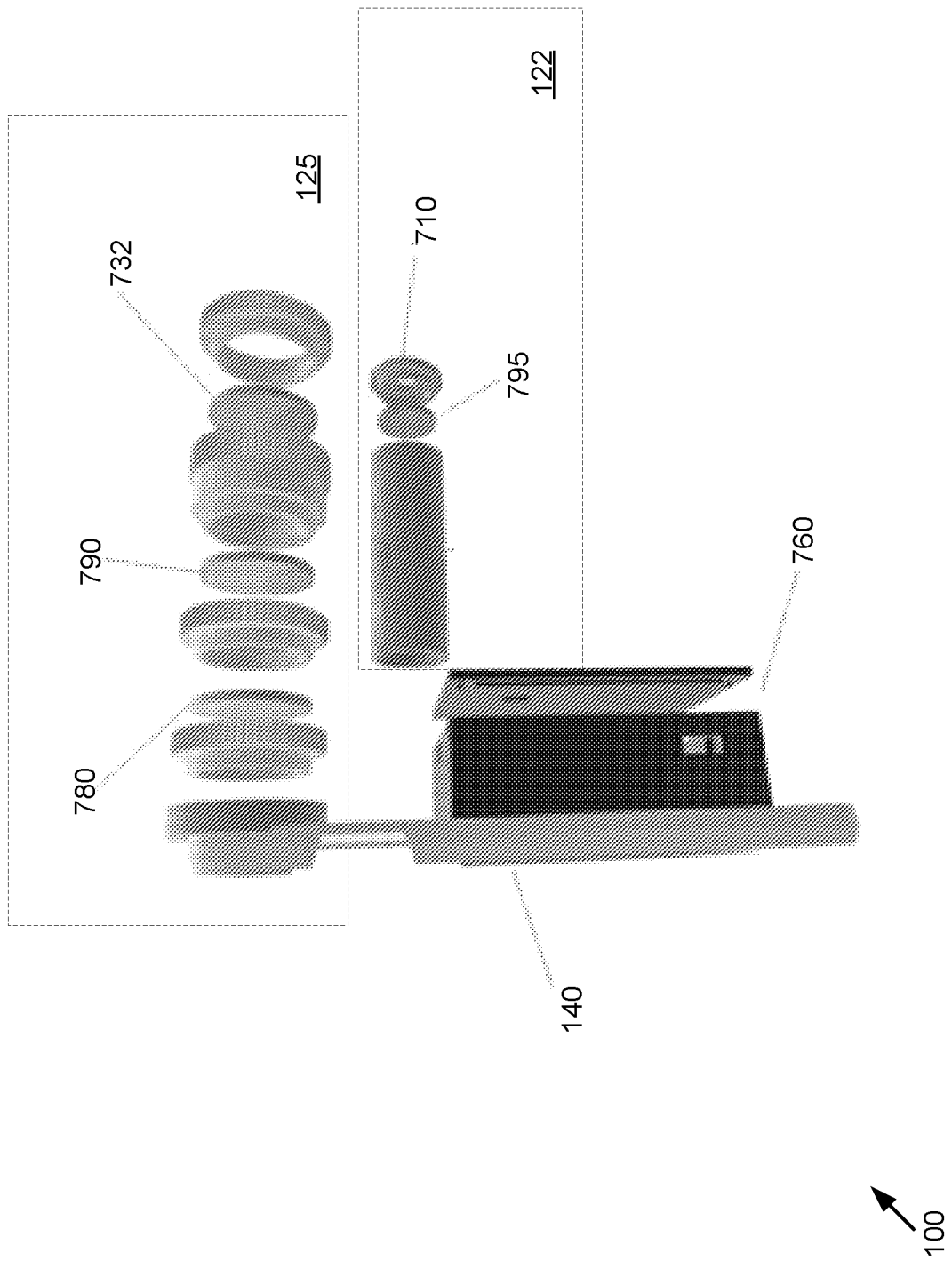
FIG. 7B is a schematic diagram of the illumination/optics device of FIG. 7A in exploded view.
Figure 8:
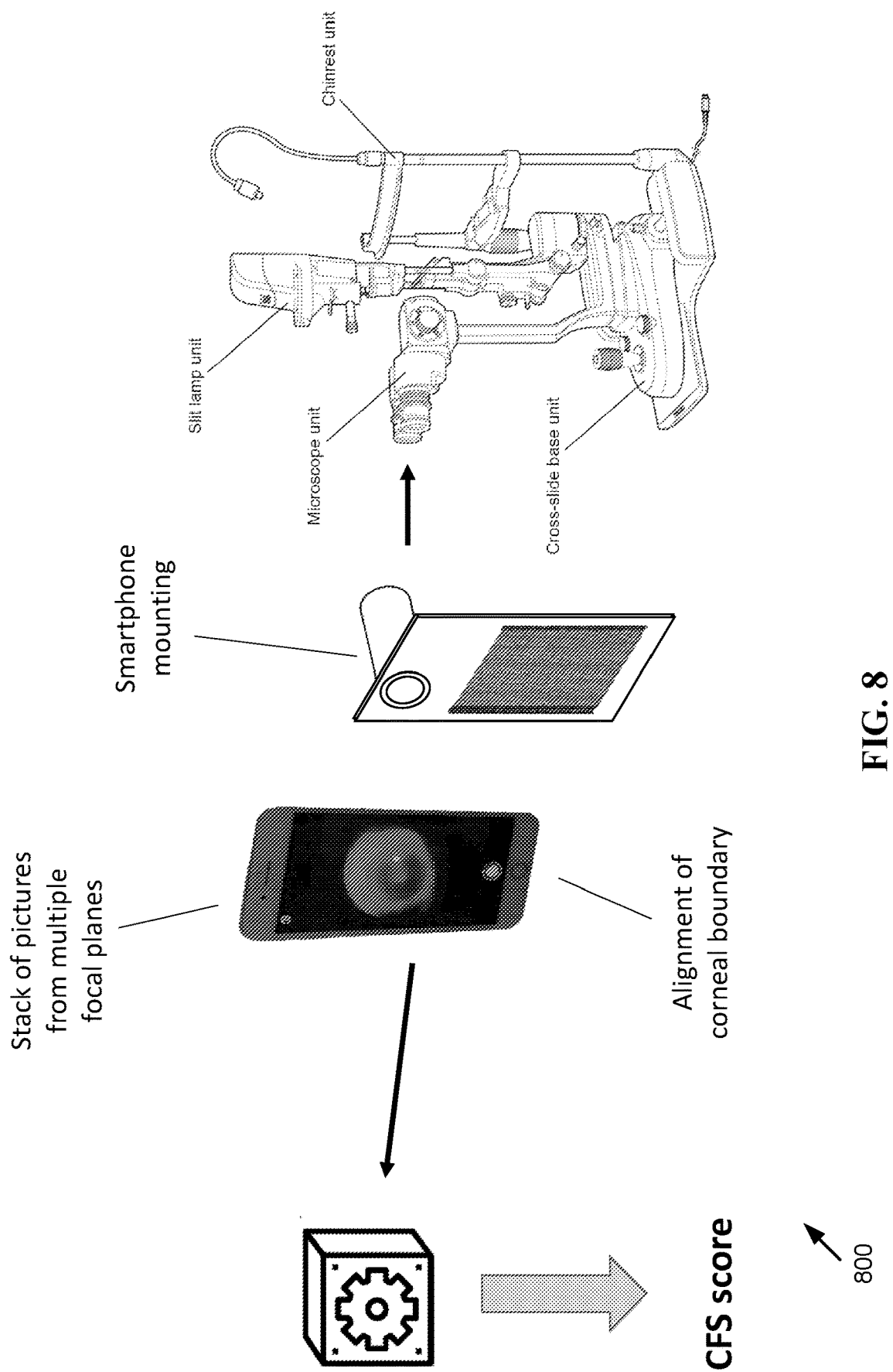
FIG. 8 is a schematic diagram of an exemplary alternative embodiment of a system for corneal image acquisition with a slit lamp attachment.

The illumination/optics device 120 (FIG. 1) may incorporate an internal slit lamp and LED light source, or may be adapted to receive light from an external slit-lamp device. FIGS. 7A-7B are a schematic diagram of an exemplary embodiment of the illumination/optics device 120 of FIG. 1. The light source 122 includes a housing for at least one white LED 738, and optionally one or more additional LEDs 736, for example emitting desired wavelengths to illuminate the cornea. A collimator lens 710 for the LED light(s) is used to concentrate the emitted light beam, for example at 15°. The light source may include one or more filters, for example, a band-pass blue filter 795 at 470 nm center wavelength. The light source 122 may be configured as a tubular housing configured to enclose optics 125 to maintain all the components in place and allow mounting on the existing smartphone 120 (or camera) case design.

The optics 125 may include an aspherized achromatic lens 732 that provides magnification in the range of 2× to 4×, for example a 3× macro magnification. An exemplary achromatic lens 732 is a 25 mm Diameter×40 mm EFL Aspherized Achromatic Lens (see https://www.edmundoptics.com/p/25 mm-diameter-x-40 mm-efl-aspherized-achromatic-lens/10169/). A telephoto zoom lens system 780 may provide additional magnification, for example, 2× magnification. The telephoto lens may be integral to the smart phone 140, or may be external to the smart phone 140. The optics 125 may include color filters, for example, a high pass yellow filter 790 at 500 nm wavelength.

The illumination/optics device 120 may include a power supply in a housing 760 attached to the smart phone 120 or a case for the smart phone 120. The power supply may be, for example, a battery-operated power source, actuated by a power switch 740 attached to, for example, the light source 122 or the power supply housing 760.

In the following exemplary implementation of CFS segmentation, a color image (RGB) and a binary mask for corneal area are received as input and the CFS segmentation provides a binary mask of CFS regions detected in the corneal regions as output.

1. The binary mask for corneal area is combined with a mask for specular reflections in the cornea to produce a modified mask.
2. The modified mask is applied to the input image, for example, by performing perform a binary AND operation.
3. After the modified mask is applied, a difference between green and blue channel is calculated as a percentage of max. gray level (255).
4. An image pyramid representation of the image is set up over a plurality of levels, for example, over four levels.
5. Wiener filtering is separately performed on each input image channel.
6. A spatial average is calculated, for example, over a 5×5 window of the filtered input image for every channel.
7. A spatial average over the 5×5 window is calculated for a difference between the green channel and the blue channel of the filtered image.
8. The average and standard deviation is computed for both spatially averaged images obtained in steps 6 and 7 the above.
9. A threshold value is set for local neighborhood difference based on the mean and standard deviation calculated in step 8,
10. Areas where large differences exist between green and blue channel are identified as candidate locations of CFS pixels. Here, a "large difference" refers to a difference is larger than a predetermined threshold percentage between the green and the blue channels, for example, the value of the green channel is on the order of 20 percent higher than the blue channel.
11. For each 25×25 block around a candidate pixel location in the averaged green component, a difference between the central 5×5 sub-block and eight peripheral 5×5 sub-blocks is calculated.
12. Instances where the difference between the central and each peripheral sub-block exceeds a neighborhood difference threshold are counted.
13. If the difference between the central and each peripheral sub-block is higher than the threshold for a majority of the blocks, a sum is included of the differences in a list for this candidate location.
14. A maximum in a histogram distribution of the sum of differences is calculated for all identified candidate locations.
15. The maximum is used as a final global threshold to compute the CFS mask.
16. Morphological operations are performed to clean up the masks.
17. Steps 5 to 16 are repeated for each subsequent level of the image pyramid.
18. A binary OR operation is performed on all the CFS mask outputs from each of the pyramid levels to obtain a final mask.

While descriptions of the embodiments above generally refer to a blue and/or green channel in RGB color space, in alternative embodiments the selected channel within the given color space may vary in accordance with the chosen tracer material and/or the color space of the acquired input image.

Figure 5:
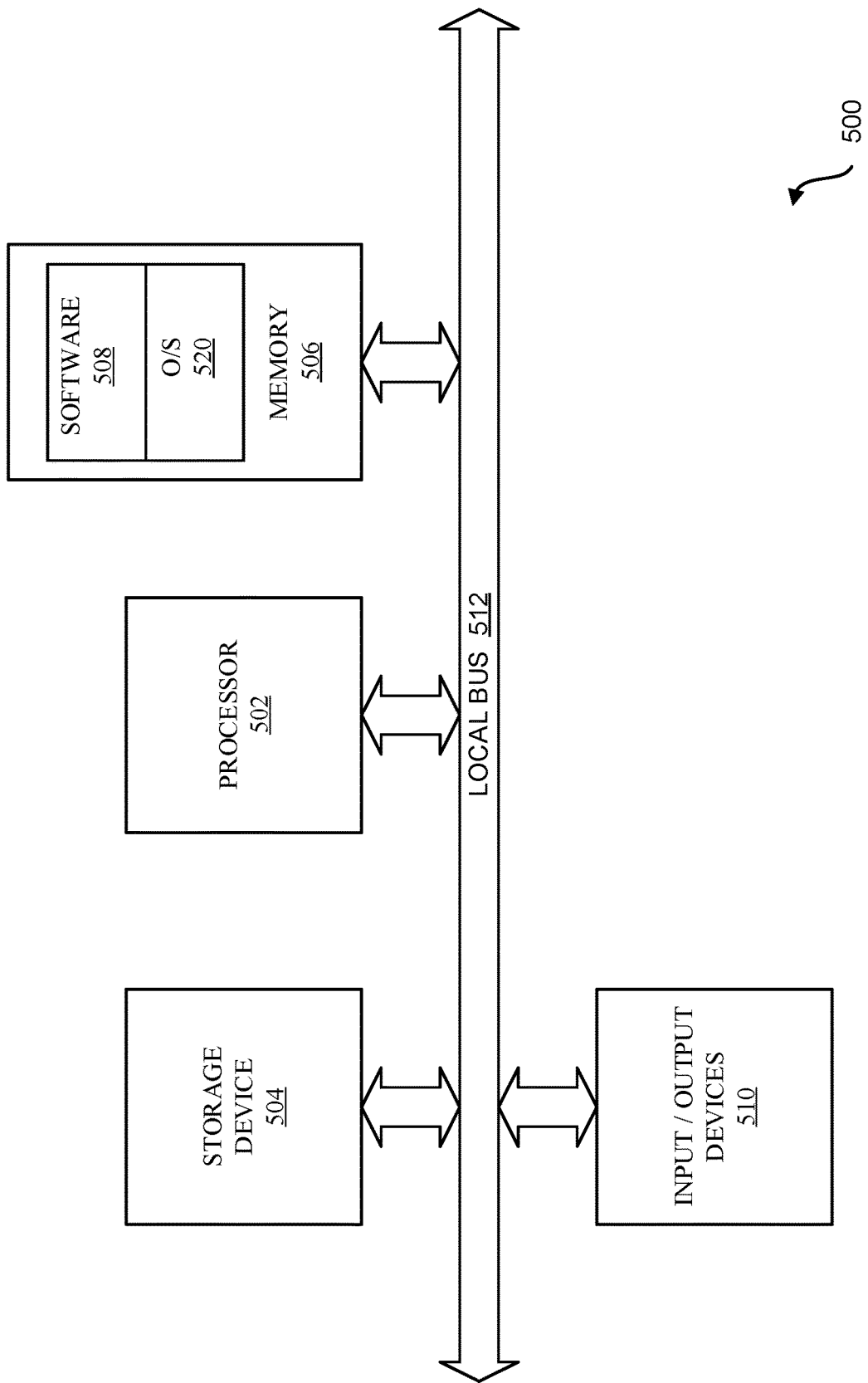
FIG. 5 is a schematic diagram illustrating an example of a system for executing functionality of the present invention.

The present system for executing the functionality described in detail above may be, for example, a computing device such as a smart phone, tablet computer, laptop computer, or desktop computer, an example of which is shown in the schematic diagram of FIG. 5. The system 500 contains a processor 502, a storage device 504, a memory 506 having software 508 stored therein that defines the abovementioned functionality, input, and output (I/O) devices 510 (or peripherals), and a local bus, or local interface 512 allowing for communication within the system 500. The local interface 512 can be, for example but not limited to, one or more buses or other wired or wireless connections, as is known in the art. The local interface 512 may have additional elements, which are omitted for simplicity, such as controllers, buffers (caches), drivers, repeaters, and receivers, to enable communications. Further, the local interface 512 may include address, control, and/or data connections to enable appropriate communications among the aforementioned components.

The processor 502 is a hardware device for executing software, particularly that stored in the memory 506. The processor 502 can be any custom made or commercially available single core or multi-core processor, a central processing unit (CPU), an auxiliary processor among several processors associated with the present system 500, a semiconductor-based microprocessor (in the form of a microchip or chip set), a macroprocessor, or generally any device for executing software instructions.

The memory 506 can include any one or combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory 506 may incorporate electronic, magnetic, optical, and/or other types of storage media. Note that the memory 506 can have a distributed architecture, where various components are situated remotely from one another, but can be accessed by the processor 502.

The software 508 defines functionality performed by the system 500, in accordance with the present invention. The software 508 in the memory 506 may include one or more separate programs, each of which contains an ordered listing of executable instructions for implementing logical functions of the system 500, as described below. The memory 506 may contain an operating system (O/S) 520. The operating system essentially controls the execution of programs within the system 500 and provides scheduling, input-output control, file and data management, memory management, and communication control and related services.

The I/O devices 510 may include input devices, for example but not limited to, a keyboard, touchscreen, mouse, scanner, microphone, etc. Furthermore, the I/O devices 510 may also include output devices, for example but not limited to, a printer, display, etc. Finally, the I/O devices 510 may further include devices that communicate via both inputs and outputs, for instance but not limited to, a modulator/demodulator (modem; for accessing another device, system, or network), a radio frequency (RF) or other transceiver, WiFi, Bluetooth, a telephonic interface, a bridge, a router, or other device.

When the system 500 is in operation, the processor 502 is configured to execute the software 508 stored within the memory 506, to communicate data to and from the memory 506, and to generally control operations of the system 500 pursuant to the software 508, as explained above.

When the functionality of the system 500 is in operation, the processor 502 is configured to execute the software 508 stored within the memory 506, to communicate data to and from the memory 506, and to generally control operations of the system 500 pursuant to the software 508. The operating system 520 is read by the processor 502, perhaps buffered within the processor 502, and then executed.

When the system 500 is implemented in software 508, it should be noted that instructions for implementing the system 500 can be stored on any computer-readable medium for use by or in connection with any computer-related device, system, or method. Such a computer-readable medium may, in some embodiments, correspond to either or both the memory 506 or the storage device 504. In the context of this document, a computer-readable medium is an electronic, magnetic, optical, or other physical device or means that can contain or store a computer program for use by or in connection with a computer-related device, system, or method. Instructions for implementing the system can be embodied in any computer-readable medium for use by or in connection with the processor or other such instruction execution system, apparatus, or device. Although the processor 502 has been mentioned by way of example, such instruction execution system, apparatus, or device may, in some embodiments, be any computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the processor or other such instruction execution system, apparatus, or device.

Such a computer-readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), a solid state drive (SSD), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted, or otherwise processed in a suitable manner if necessary, and then stored in a computer memory.

In an alternative embodiment, where the system 500 is implemented in hardware, the system 500 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The above described embodiments provide important advantages compared to previous approaches:

- smartphone camera directly attaches to the optic system without degrading the image quality.
- Guided and quick alignment of the lens.
- Image acquisition software to guide the user and standardize the image acquisition process for more reliable comparisons among different acquisitions.
- Image processing software that provides a staining score with medical value for the monitoring of ocular surface conditions.
- Image acquisition and processing accounts for corneal curvature and depth.

The interpolation of the pixels in the multi-layered image acquisition with increased depth of focus can be alternatively achieved with weights $W_D$ that follow an exponential biquadratic equation as per Eq. 2:

$$w_D = e^{-\frac{\left(x - \frac{D}{N}\right)^4}{a}}$$

where D is the index of the weight, N is the number of images acquired, and a is a factor proportional to the full width at half maximum of the function.

The image processing modules may include a classification module that uses a previously trained neural network. Such a module distinguishes between pixels excited by the fluorescein and pixels that are not reacting to the dye (healthy portions of the cornea).

Alternative embodiments may provide quantification of a variety of color-dependent ocular surface features via custom-tailored image processing modules to fit the appropriate color channels. For instance, 1) corneal and conjunctival staining with dyes other than fluorescein (e.g., lissamine green, rose Bengal) or no dyes at all, 2) with light sources of different colors or white light, 3) presenting shapes other than circles in the guided image-acquisition protocol to easily select areas of the ocular surface different to the cornea (e.g., a triangular shape to fit the nasal conjunctiva).

Alternative embodiments may provide different values to different regions of the cornea (score weight) in relation with their clinical importance, for example, more weight to the pupil area and visual axis, or where the disease can interfere more with vision, to establish a score that is more clinically significant and representative of the corneal damage. In this weighted grading system, superior regions of the cornea might be disregarded or receive a very low weight in the score.

The weighted clinical significance score may incorporate variables such as type of diagnosis, age, environmental factors (humidity, climate), race, gender, professional activity, hours of computer or screen use, and other clinically-significant variables. The score can be tailored based on the intended practical application of the scoring system: e.g., clinical trials, initial diagnosis of the corneal condition, routine medical examinations, etc. The clinical significance score can be correlated with the medical diagnosis in order to provide an assisted automated diagnosis through machine-learning algorithms.

In further embodiments, the conjunctival staining grading feature may be used to complement the CFS and ocular surface clinical significance scores. The disease in the clinical significance score does not necessarily have to be a primarily ocular condition, but may be a systemic disorder (e.g., diabetes, dermatological condition, etc.) that concurs with ocular surface involvement.

The diversity of mechanisms underlying ocular surface disease and the expected variation in patient responses fuel the development of numerous additional ocular surface disease therapeutics, and drug makers have responded with several candidates in the pipeline. A standardized and objective scoring system with finer, continuous scale increments provided by the embodiments described herein may facilitate ocular surface disease-related clinical trials and accelerate the commercial availability of novel efficacious drugs. In the absence of novel drugs for ocular surface disease, corneal specialists faced with severe ocular surface disease cases resort to off-label applications of topical or oral medicines, custom-prepared and perishable eye drop preparations derived from the patient's own blood or other interventions. Such therapeutic approaches can be time-consuming, costly, and in many cases not reimbursed by insurers, becoming a major economic burden on patients and the healthcare system. Easily scalable and deployable technology for objective CFS measurement may provide less variability in the outcome measures, an agile and consistent approach in multi-center studies, and ultimately reduce costs and time for the approval of new therapies.

After the initial management of ocular surface disease, patients may experience a wide variety of changes, including favorable or unfavorable responses to specific treatments. Thus, medical management should be conducted and monitored regularly by an expert clinician. The typical monitoring frequency is every 6 months, but a higher frequency, possibly every 1-3 months, would improve care. However, frequent clinic visits may conflict with the patient's time and financial constraints, posing challenges to the optimal delivery of care. Unmonitored and untreated severe dry eye disease can result in scarring, ulceration, infection, and even perforation of the cornea, which is critical to eye health and clear vision. Optimal ocular surface disease monitoring and improved management among non-specialized ocular surface disease eye care providers could be significantly improved with the new scalable and objective test to be administered by non-trained personnel and general healthcare practitioners.

The smartphone-based technology of the embodiments described herein may reduce variability and improve access and delivery of medical care. In other cases, people with chronic conditions such as diabetes can present clinical signs of ocular surface disease (e.g., CFS) without symptoms. In such cases, it may be difficult for doctors to determine if this is due to variability in the previous CFS scoring system or to actual changes in corneal epithelium, which creates confusion and complicates therapeutic management. Corneal specialists face additional challenges delivering clinical care to patients in rural or underserved areas where local care providers may not have enough experience. In both situations, the present embodiments may provide much needed consistent and objective results.

While the embodiments described above are drawn to the example of scoring CFS, the invention is also applicable to other areas of the ocular surface, for example, but not limited to conjunctival staining. For example, plain white light may be used in some cases of conjunctival imaging where a green dye is used instead of yellow). When using a green dye (lissamine green), the processing may use a different color channel. Three dyes commonly used include fluorescein, lissamine green, and rose Bengal.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A system for determining a staining score of a cornea and/or adjacent areas portions within the ocular surface of a subject with dyeable epithelia, comprising:
    a portable computing device further comprising a camera, a display, a memory, and a processor, wherein the memory is configured to store non-transient instructions for a staining score application;
    an illumination/optics device comprising a light source and optics configured to receive an image comprising the cornea; and
    attachment means configured to removably attach the illumination/optics device to the portable computing device,
    wherein the staining score application further comprises:
        an alignment module;
        an image acquisition module; and
        a staining scoring module.

2. The system of claim 1, wherein the portable computing device is of one of the group consisting of a smart phone, a tablet computer, a desktop computer, and a laptop computer.

3. The system of claim 1, wherein the image acquisition module further comprises a cornea detection module and a blur detection module.

4. The system of claim 1, wherein the alignment module is configured to align a camera according to a cornea of the subject.

5. The system of claim 1, wherein the image acquisition module is configured to acquire a plurality of ocular images of the subject with a camera.

6. The system of claim 1, wherein the staining scoring module is configured to determine a staining score of a cornea and/or adjacent areas portions within the ocular surface of a subject from a plurality of ocular images.

7. The system of claim 1, wherein staining score application is at least partially hosted by a remote server.

8. A computer-based method for aligning a camera to acquire an ocular image of a subject, comprising the steps of:
    displaying a live image preview of the cornea;
    calculating and storing a projected light dimension in pixels Dc;
    detecting a change in focus of the live image preview;
    overlaying a projected light shape on the live image preview; and
    prompting a user to acquire the ocular image when Dc is equal to a horizontal dimension D of the projected light upon a calibration pattern.

9. The method of claim 8, further comprising the step of calibrating the camera by determining the horizontal dimension D of the projected light upon a calibration pattern.

10. A computer-based method for acquiring a plurality of ocular images comprising a cornea and/or adjacent areas portions within the ocular surface of a subject with a camera, comprising the steps of:
    detecting an actuation of a camera shutter;
    automatically adjusting the camera to a plurality of focal distances corresponding to the plurality of images;
    calculating a region of interest for each image of the plurality of images;
    calculating a blur region for each image of the plurality of images;
    calculating an overall light level of the plurality of images Lsc;
    for each image, comparing an overall blur score Bsc, an exposed area of the cornea Cv and Lsc against predetermined thresholds; and
    calculating a binary quality score according to the threshold comparison.

11. The method of claim 10, wherein calculating the region of interest for each image of the plurality of images further comprises the steps of:
    calculating a cornea detection reliability score;
    translating cornea dimensions from pixels to size units;
    comparing the calculated cornea size to a threshold Cth for deviation from an average human cornea size;
    calculating and storing an exposed area of the cornea Cv; and
    recording a binary mask for a region of interest at each intersection of the cornea and the eyelid.

12. The method of claim 10, further comprising the step of replacing an image having a non-satisfactory quality score.

13. The method of claim 10, wherein calculating the blur region for each image of the plurality of images further comprises the steps of:
    calculating a first derivative utilizing spatial windows;
    storing an area of blur as a binary blur mask; and
    calculating and storing an overall blur score Bsc for each image.

14. The method of claim 10, wherein the region of interest corresponds to an intersection of the cornea and an eyelid of the subject.

15. A method for determining a staining score of a cornea and/or adjacent areas portions within the ocular surface of a subject from a plurality of ocular images, comprising the steps of:
    intersecting a region of interest ocular mask with a blur ocular mask of an ocular image of the plurality of ocular images;
    calculating and normalizing a difference between a first color channel and a second color channel for all pixels;
    applying a threshold based on a mean and a standard deviation of differences between the first color channel and the second channel;
    generating a plurality of ocular masks with pixels identified as stained for a corresponding plurality of resolutions;

forming a combined mask by combining the staining mask for each of the images obtained across a plurality of resolutions at different focal depths;
identifying stained pixels in the combined mask;
calculating a number of pixels identified as stained in the combined mask; and
generating the staining score according to a proportion of stained pixels to unstained pixels.

16. The method of claim 15, wherein the plurality of resolutions range from as large as 3024×4032 to as small as 379×504.

17. The method of claim 15, wherein the first color channel is green and the second color channel is blue.

* * * * *